(12) United States Patent
Tipirneni

(10) Patent No.: US 7,901,412 B2
(45) Date of Patent: *Mar. 8, 2011

(54) METHOD FOR THE FIXATION OF BONE STRUCTURES

(75) Inventor: Kishore Tipirneni, Glendale, AZ (US)

(73) Assignee: Orthoip, LLC, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/400,184

(22) Filed: Mar. 9, 2009

(65) Prior Publication Data

US 2009/0171403 A1 Jul. 2, 2009

Related U.S. Application Data

(60) Division of application No. 10/779,892, filed on Feb. 17, 2004, now Pat. No. 7,591,823, which is a continuation of application No. 10/272,773, filed on Oct. 17, 2002, now Pat. No. 6,736,819.

(60) Provisional application No. 60/330,187, filed on Oct. 18, 2001.

(51) Int. Cl.
*A61B 17/58* (2006.01)
*A61B 17/86* (2006.01)

(52) U.S. Cl. ......... 606/103; 606/105; 606/301; 606/305; 606/318; 606/320

(58) Field of Classification Search ............... 606/103
See application file for complete search history.

(56) References Cited

U.S. PATENT DOCUMENTS

| | | | |
|---|---|---|---|
| 2,077,804 A | 4/1937 | Morrison | |
| 2,511,051 A | 6/1950 | Dzus | |
| 3,051,169 A | 8/1962 | Gustaf-Bertil | |
| 3,489,143 A | 1/1970 | Halloran | |
| 4,621,629 A | 11/1986 | Koeneman | |
| 4,640,271 A | 2/1987 | Lower | |
| 4,858,601 A | 8/1989 | Glisson | |
| 4,863,383 A | 9/1989 | Grafelmann | |
| 4,934,935 A | 6/1990 | Edwards | |
| 4,940,467 A | 7/1990 | Tronzo | |
| 4,959,064 A | 9/1990 | Engelhardt | |
| 5,041,116 A | 8/1991 | Wilson | |

(Continued)

FOREIGN PATENT DOCUMENTS

WO WO2007125561 11/2007

(Continued)

OTHER PUBLICATIONS

Final Office Action issued Jan. 22, 2010 in U.S. Appl. No. 11/742,457.

(Continued)

*Primary Examiner* — David H Willse
*Assistant Examiner* — Javier G Blanco
(74) *Attorney, Agent, or Firm* — Snell & Wilmer L.L.P.

(57) ABSTRACT

The invention facilitates the fixation of bone fractures. In a particular embodiment, a method for fixing bone fractures comprises the steps of: inserting a head component coupled to a wire through a first bone portion and anchoring the head component in a second bone portion, inserting a cap over the wire toward the head component until the cap contacts the second bone portion, and applying pressure to the wire using a tensioner to reduce the distance between the first bone portion and the second bone portion. The excess wire beyond the cap can then be removed.

7 Claims, 4 Drawing Sheets

U.S. PATENT DOCUMENTS

| | | |
|---|---|---|
| 5,061,137 A | 10/1991 | Gourd |
| 5,102,276 A | 4/1992 | Gourd |
| 5,116,336 A | 5/1992 | Frigg |
| 5,116,340 A | 5/1992 | Songer et al. |
| 5,122,133 A | 6/1992 | Evans |
| 5,127,914 A | 7/1992 | Calerate et al. |
| 5,129,901 A | 7/1992 | Decoste |
| 5,141,520 A | 8/1992 | Goble et al. |
| 5,217,462 A | 6/1993 | Asnis et al. |
| 5,300,075 A | 4/1994 | Gordon |
| 5,324,292 A | 6/1994 | Meyers |
| 5,336,028 A | 8/1994 | Yamamoto |
| 5,338,139 A | 8/1994 | Swanstrom |
| 5,382,124 A | 1/1995 | Frattorola |
| 5,431,660 A | 7/1995 | Burke |
| 5,462,547 A | 10/1995 | Weigum |
| 5,507,801 A | 4/1996 | Gisin |
| 5,520,691 A | 5/1996 | Branch |
| 5,586,985 A | 12/1996 | Putnam et al. |
| 5,709,687 A | 1/1998 | Penning |
| 5,809,849 A | 9/1998 | Coffey et al. |
| 5,810,821 A | 9/1998 | Vandewalle |
| 5,827,285 A | 10/1998 | Bramlet |
| 5,893,850 A | 4/1999 | Cachia |
| 5,893,859 A | 4/1999 | Marin et al. |
| 5,899,906 A | 5/1999 | Schenk |
| 5,902,011 A | 5/1999 | Hand et al. |
| 5,954,722 A | 9/1999 | Bono |
| 5,964,763 A | 10/1999 | Incavo et al. |
| 5,976,139 A | 11/1999 | Bramlet |
| 5,984,925 A | 11/1999 | Apgar |
| 5,993,477 A | 11/1999 | Vaitekunas et al. |
| 5,997,538 A | 12/1999 | Asnis et al. |
| 5,997,541 A | 12/1999 | Schenk |
| 6,039,740 A | 3/2000 | Olerud |
| 6,050,998 A | 4/2000 | Fletcher |
| 6,093,188 A | 7/2000 | Murray |
| 6,171,310 B1 | 1/2001 | Giordano |
| 6,174,006 B1 | 1/2001 | Burt |
| 6,183,474 B1 | 2/2001 | Bramlet |
| 6,235,062 B1 | 5/2001 | Grammas |
| 6,245,071 B1 | 6/2001 | Pierson |
| 6,251,111 B1 | 6/2001 | Barker et al. |
| 6,348,053 B1 | 2/2002 | Cachia |
| 6,368,326 B1 | 4/2002 | Dakin et al. |
| 6,602,293 B1 | 8/2003 | Biermann et al. |
| 6,610,067 B2 | 8/2003 | Tallarida et al. |
| 6,632,224 B2 | 10/2003 | Cachia et al. |
| 6,656,184 B1 | 12/2003 | White et al. |
| 6,685,706 B2 | 2/2004 | Padget et al. |
| 6,695,844 B2 | 2/2004 | Bramlet |
| 6,840,953 B2 | 1/2005 | Martinek |
| 6,887,243 B2 | 5/2005 | Culbert |
| 6,887,271 B2 | 5/2005 | Justin et al. |
| 6,890,333 B2 | 5/2005 | von Hoffmann et al. |
| 6,908,465 B2 | 6/2005 | von Hoffmann et al. |
| 6,984,241 B2 | 1/2006 | Lubbers et al. |
| 7,008,428 B2 | 3/2006 | Cachia et al. |
| 7,033,363 B2 | 4/2006 | Powell |
| 7,070,601 B2 | 7/2006 | Culbert et al. |
| 7,090,676 B2 | 8/2006 | Huebner et al. |
| 7,094,240 B2 | 8/2006 | Molz et al. |
| 7,135,023 B2 | 11/2006 | Watkins |
| 7,147,639 B2 | 12/2006 | Berki et al. |
| 7,163,542 B2 | 1/2007 | Ryan |
| 7,172,595 B1 | 2/2007 | Goble |
| 7,189,251 B2 | 3/2007 | Kay |
| 7,476,254 B2 | 1/2009 | White et al. |
| 7,591,823 B2 | 9/2009 | Tipirneni |
| 7,641,677 B2 | 1/2010 | Weiner et al. |
| 7,771,428 B2 | 8/2010 | Siravo et al. |
| 2002/0198527 A1 | 12/2002 | Muckter |
| 2003/0036761 A1 | 2/2003 | Smothers et al. |
| 2003/0216780 A1 | 11/2003 | Fitts et al. |
| 2004/0097943 A1 | 5/2004 | Hart |
| 2004/0236424 A1 | 11/2004 | Berez et al. |
| 2005/0263549 A1 | 12/2005 | Scheiner |
| 2006/0129148 A1 | 6/2006 | Simmons et al. |
| 2006/0147127 A1 | 7/2006 | Slavin |
| 2006/0161805 A1 | 7/2006 | Tseng |
| 2006/0190001 A1 | 8/2006 | Powell |
| 2007/0055249 A1 | 3/2007 | Jensen |
| 2007/0123878 A1 | 5/2007 | Shaver |
| 2007/0162019 A1 | 7/2007 | Burns |
| 2007/0162026 A1 | 7/2007 | Tipernini et al. |
| 2007/0190230 A1 | 8/2007 | Trieu |
| 2007/0260248 A1 | 11/2007 | Tipirneni |
| 2007/0270847 A1 | 11/2007 | Shaw |
| 2007/0276382 A1 | 11/2007 | Mikhail et al. |
| 2008/0147126 A1 | 6/2008 | Tipirneni |
| 2008/0243191 A1 | 10/2008 | Tipernini et al. |
| 2008/0255555 A1 | 10/2008 | Justis et al. |
| 2008/0255621 A1 | 10/2008 | Fricker et al. |
| 2008/0300636 A1 | 12/2008 | Carli et al. |
| 2009/0131936 A1 | 5/2009 | Tipernini et al. |
| 2009/0131990 A1 | 5/2009 | Tipernini et al. |
| 2009/0131991 A1 | 5/2009 | Tipernini et al. |
| 2009/0177199 A1 | 7/2009 | Tipirneni |
| 2009/0198288 A1 | 8/2009 | Hoof et al. |
| 2009/0254089 A1 | 10/2009 | Tipirneni |
| 2009/0254129 A1 | 10/2009 | Tipirneni |
| 2009/0306718 A1 | 12/2009 | Tipirneni |
| 2010/0114097 A1 | 5/2010 | Siravo et al. |

FOREIGN PATENT DOCUMENTS

| | | |
|---|---|---|
| WO | WO2009015075 | 12/2009 |

OTHER PUBLICATIONS

Non-Final Office Action issued Dec. 30, 2009 in U.S. Appl. No. 11/952,413.
Final Office Action issued Jan. 25, 2010 in U.S. Appl. No. 11/952,715.
PCT/US2009/061782 International Search Report and Written Opinion issued Dec. 15, 2009.
PCT/US09/578791 International Search Report and Written Opinion issued Nov. 15, 2009.
U.S. Appl. No. 10/779,892 Office Action dated Nov. 16, 2005.
U.S. Appl. No. 10/779,892 Office Action dated Apr. 26, 2006.
U.S. Appl. No. 10/779,892 Office Action dated Jul. 18, 2006.
U.S. Appl. No. 10/779,892 Office Action dated Oct. 11, 2006.
U.S. Appl. No. 10/779,892 Final Office Action dated Jan. 3, 2007.
U.S. Appl. No. 10/779,892 Office Action dated Feb. 2, 2007.
U.S. Appl. No. 10/779,892 Office Action dated Mar. 1, 2007.
U.S. Appl. No. 10/779,892 Office Action dated Aug. 8, 2007.
U.S. Appl. No. 10/779,892 Final Office Action dated Oct. 31, 2007.
U.S. Appl. No. 10/779,892 Advisory Action dated Jan. 22, 2008.
U.S. Appl. No. 10/779,892 Office Action dated Mar. 4, 2008.
U.S. Appl. No. 10/779,892 Office Action dated Aug. 29, 2008.
U.S. Appl. No. 10/779,892 Office Action dated Dec. 10, 2008.
U.S. Appl. No. 10/272,773 Office Action dated Nov. 19, 2003.
Notice of Allowance mailed Feb. 20, 2004 in U.S. Appl. No. 10/272,773.
ISR and Written Opinion mailed Jan. 22, 2009 in PCT/US08/84623.
Final Office Action mailed May 14, 2009 in U.S. Appl. No. 10/779,892.
Notice of Allowance mailed Aug. 7, 2009 in U.S. Appl. No. 10/779,892.
Non-Final Office Action mailed Aug. 6, 2009 in U.S. Appl. No. 11/742,457.
Non-Final Office Action mailed Jun. 10, 2009 in U.S. Appl. No. 11/952,413.
Non-Final Office Action mailed Jun. 19, 2009 in U.S. Appl. No. 11/952,715.
Non-Final Office Action mailed Aug. 20, 2009 in U.S. Appl. No. 11/678,473.
Final Office Action issued Jun. 29, 2010 in U.S. Appl. No. 11/952,413.
Advisory Action issued Sep. 1, 2010 in U.S. Appl. No. 11/952,413.
PCT International Search Report and Written Opinion dated Jan. 22, 2009.
Final Office Action mailed Feb. 19, 2010 in U.S. Appl. No. 11/678,473.

Advisory Acton mailed Apr. 14, 2010 in U.S. Appl. No. 11/678,473.
Final Office Action mailed Jan. 22, 2010 in U.S. Appl. No. 11/742,457.
Advisory Action mailed Mar. 30, 2010 in U.S. Appl. No. 11/742,457.
Final Office Action mailed Jan. 25, 2010 in U.S. Appl. No. 11/952,715.
Advisory Action mailed on Apr. 12, 2010 in U.S. Appl. No. 11/952,715.

Notice to File Missing Parts on May 12, 2010 in U.S. Appl. No. 12/769,529.

URL: http://www.cayennemedical.com/products/ifix/, Title: iFix, Source: Cayenne Medical, Jan. 15, 2009.

PCT-US2010-023537 International Search and Written Opinion Report mailed Apr. 15, 2010.

METHOD FOR THE FIXATION OF BONE STRUCTURES

CROSS-REFERENCE TO RELATED APPLICATIONS

This application is a divisional of, and claims priority to, and the benefit of, U.S. Ser. No. 10/779,892, filed on Feb. 17, 2004 and entitled "SYSTEM AND METHOD FOR THE FIXATION OF BONE FRACTURES," which itself is a continuation of, and claims priority to, U.S. Ser. No. 10/272,773, filed on Oct. 17, 2002 with the same title (now U.S. Pat. No. 6,736,819). The '819 patent itself claims priority to U.S. Provisional Application Ser. No. 60/330,187, filed on Oct. 18, 2001 and entitled "LAGWIRE SYSTEM AND METHOD." All of the above-mentioned patents and applications are incorporated herein by reference in their entirety.

FIELD OF INVENTION

The invention generally relates to a system and method for the fixation of fractures in one or more objects, and more particularly, to a lagwire system and related components for the fixation of bone fractures.

BACKGROUND OF THE INVENTION

It is well-known in the medical arts that constant pressure on a bone fracture speeds healing. As such, orthopedic physicians typically insert one or more screws in the area of the fracture in order to assert constant pressure on the bone fracture. However, the insertion of existing screws through or around fractures has disadvantages. For example, the entire process is very time-consuming because inserting a regular screw usually involves multiple steps such as drilling the pilot hole, measuring the relevant distances to determine the appropriate screw selection, tapping the hole to establish threads and screwing the screw into the hole. Moreover, when using a lagscrew, the process usually includes even more steps such as drilling through the near cortex to establish the gliding hole (e.g., 3.5 mm), placing the drill guide in the proper location, drilling through the far cortex (e.g., 2.5 mm), measuring the distance to determine the appropriate screw selection, tapping the hole to establish threads and screwing the screw into the hole, thereby attempting to compress the fracture. Again, each step and the entire process is very time-consuming.

In addition to the length and complexity of the process, the prior art system also typically includes inadequate components. For example, in poor bone, prior art screws often loose their grip and strip out of the bone. Currently available lag screws also typically provide only one side of cortex fixation and are generally not suited for percutaneus surgery. Moreover, when placing the screws in the bone, the physician may not accurately set the screw into the distal hole or may miss the distal hole completely, thereby resulting in the screw stripping the threads or breaking the bone.

Furthermore, the location and extent of most every fracture is unique, so different screws are often needed for each fracture. Because the physician typically is unable to accurately determine the type or size of screw needed until the physician enters the bone and measures the appropriate screw placement, operating facilities need to store and make available large inventories of screws. Particularly, screws usually range in length from about 10 mm to about 75 mm with available screw sizes limited to every 2 mm there between. Moreover, for each size of screw, the screws may be either a cancellous or cortical type, and for each size and type of screw, the screw may include one of three different pitches. Accordingly, a screw set typically exceeds one hundred screws. Furthermore, if cannulated screws are desired, another entire screw set of over one hundred additional screws is often needed. Moreover, each time a screw from a screw set is utilized in a procedure, a replacement screw is typically obtained to complete the set. As such, inventory management of screws is a very large problem for many operating facilities. A need exists for a lagwire system which simplifies and expedites the process for the fixation of bone fractures, while minimizing the number of components needed in the process.

SUMMARY OF THE INVENTION

In general, the invention facilitates the fixation of bone fractures. In an exemplary embodiment, a method for fixing bone fractures includes the steps of: providing a head component affixed to a flexible wire having a first interface component, inserting the head component into a first surface and translating a cap, without rotation of said cap, over an end portion of a flexible wire into a second surface.

In various embodiments, a method for fixing bone fractures includes the steps of: inserting a head component coupled to a wire through a first bone portion and anchoring the head component in a second bone portion, inserting a cap over the wire toward the head component until the cap contacts the second bone portion, and applying pressure to the wire using a tensioner to reduce the distance between the first bone portion and the second bone portion.

BRIEF DESCRIPTION OF THE DRAWINGS

A more complete understanding of the present invention may be derived by referring to the detailed description and claims when considered in connection with the figures, wherein like reference numbers refer to similar elements throughout the figures, and:

DETAILED DESCRIPTION

The present invention is described herein and includes various exemplary embodiments in sufficient detail to enable those skilled in the art to practice the invention, and it should be understood that other embodiments may be realized without departing from the spirit and scope of the invention. Thus, the following detailed description is presented for purposes of illustration only, and not of limitation, and the scope of the invention is defined solely by the appended claims. The particular implementations shown and described herein are illustrative of the invention and its best mode and are not intended to otherwise limit the scope of the present invention in any way.

In general, the present invention facilitates the change in distance between objects or surfaces, compresses objects together and/or provides a configurable or random amount of pressure between surfaces. The system may facilitate changing, maintaining, reducing and/or expanding the distance between objects. The applied pressure may be suitably configured to be constant, increasing, decreasing, variable, random, and/or the like. In an exemplary embodiment, the invention includes a device which may be fixedly or removably attached to pathology, such as to a certain portion of a bone. In a particular embodiment, the device is fixedly or removably attached to the far cortex of the bone. In another embodiment, the invention includes a device or method for retracting the attached device to reduce the distance between the surfaces of the pathology. In a further embodiment, the invention includes a device and/or method for maintaining the pressure between the surfaces of pathology.

Figure 1:
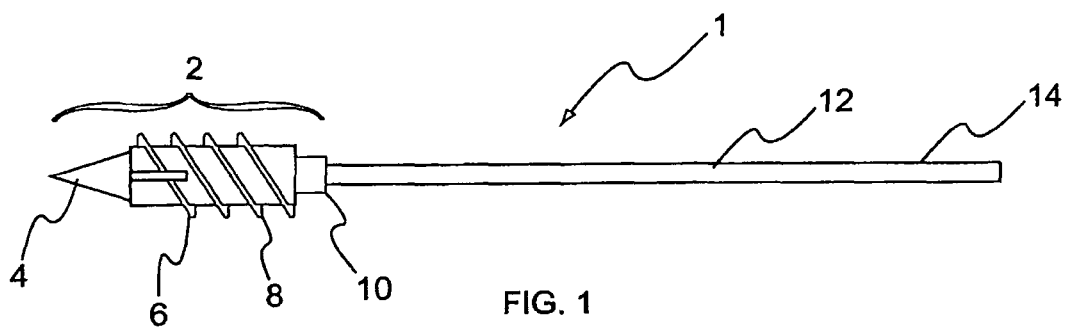
FIG. 1 is a lagwire system comprising a head component and wire in accordance with an exemplary embodiment of the present invention.

In an exemplary embodiment, and as shown in FIGS. 1 and 2, the lagwire system 1 includes a head component 2, a wire 12 and a cap 20. The lagwire system 1 may be fabricated using any type, amount or combination of materials suitably configured for the particular application. In an exemplary embodiment for medical applications, the lagwire system 1 is fabricated with stainless steel, titanium and/or titanium alloy which minimize reactivity with the body. Each component may be fabricated with various diameters, thread pitches, lengths and/or the like.

Certain exemplary components of the system will now be discussed. The head component 2 is any device which is configured to fixedly or removably attach to any object, such as pathology. In a particular embodiment, the head component 2 is configured to be fixedly or removably attached to the far cortex of the bone, as shown in FIGS. 4A-4G. As best shown in FIG. 1, the head component 2 may include, for example, a self drilling tip 4 device which is suitably configured to puncture a hole and/or guide the head component 2, self cutting threads 6 which are suitably configured to cut thread grooves into the inside surface of a hole, fastening threads 8 which are suitably configured to mate with the newly formed thread grooves, and a tool attachment 10 suitably configured for mating with a tool head (e.g., hex head wrench, socket wrench, Phillips screwdriver, flathead screwdriver, allan wrench and/or the like).

In a particular embodiment, the tip is on the front end of head component 2, followed by the cutting threads 6, the fastening threads 8, the tool attachment 10, then wire 12. The elements of head component 2 may be fabricated as one component or one or more elements may be configured to be removably or fixedly mated together to form head component 2. If mated together, a particular element may be exchanged for different applications. For example, if head component 2 needs to be inserted into a dense or hard bone, a stronger or sharper tip 4 may be screwed into thread element 6,8. Moreover, if deeper thread grooves are desired, cutting threads 6 may be replaced with greater diameter threads. Furthermore, if a different tool head is incorporated into a drill, tool attachment 10 may be exchanged with the appropriate attachment.

In one embodiment, the outside diameter of the fastening threads are similar to the thread diameters of known surgical screw sizes. Exemplary outside diameters of cortical head components include 3.5 mm and 4.5 mm, wherein the length of the thread section is similar to the cortex thickness. Exemplary outside diameters of cancellous (i.e., little or no cortex) head components include about 4.0 mm and 6.5 mm, wherein the length of the thread section may be about 16 mm or 32 mm.

Wire 12 is any device suitably configured, when tension is applied, to reduce the distance between two surfaces. In one embodiment, wire 12 is configured to retract the head component 2 device to reduce the distance between the surfaces of the pathology. In one embodiment, head component 2 and wire 12 are constructed as one component. In another embodiment, head component 2 and wire 12 are constructed as separate components, but the components are configured such that the head component 2 may be threaded onto wire 12 after wire 12 is placed into the bone. Wire 12 further includes an interface component 14 on at least a portion of its surface, wherein the interface component 14 is suitably configured to limit the movement of cap 20 to move distally toward head component 2, but not proximally (backwards). In an exemplary embodiment, interface component 14 of wire 12 includes a sawtooth like configuration such that one side of each tooth (e.g. the side closest to head component 2) is substantially perpendicular to the surface of wire 12, while the other side of the sawtooth is at a suitable angle, such as 45 degrees, thereby forming a triangular pattern for each sawtooth. In this manner, the inverse sawtooth on the inside surface of the cap slides or bends over the angled side of the wire sawtooth, but the substantially perpendicular side of the wire sawtooth restricts or limits the cap sawtooth from backwards movement.

In an exemplary embodiment, wire 12 is comprised of a thin metal such as, for example, stainless steel, titanium and/or titanium alloy, so it may be easily cut to almost any desired length, thereby eliminating or reducing the need for fixed lengths screws. As such, the invention substantially reduces or eliminates the need for the inventory or availability of large screw sets or multiple screws. Moreover, because the system may include numerous materials, configurations and designs for either wire 12 or cap 20, the invention provides increased versatility because the physician is provided with multiple options and choices for wire 12 and cap 20 combinations.

Figure 2A:
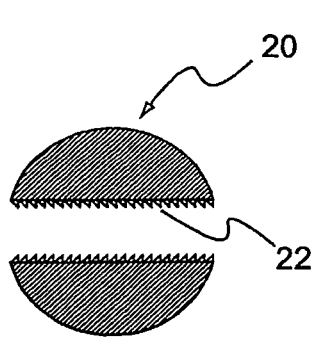
FIG. 2A is a quick cap in accordance with an exemplary embodiment of the present invention.
Figure 2B:
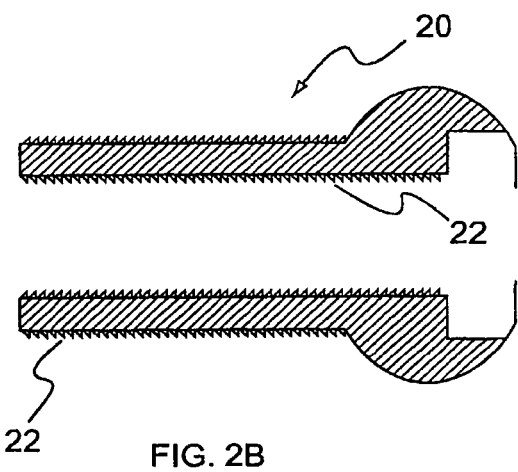
FIG. 2B is an alternative embodiment of a quick cap in accordance with an exemplary embodiment of the present invention.
Figure 2C:
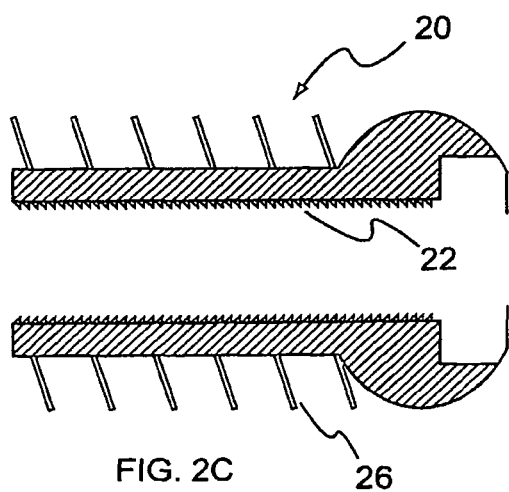
FIG. 2C is a screw cap in accordance with an exemplary embodiment of the present invention.
Figure 2D:
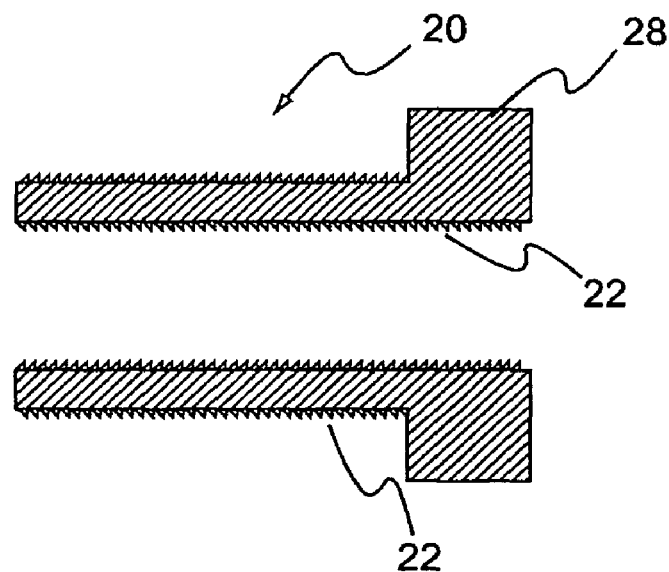
FIG. 2D is a flat cap in accordance with an exemplary embodiment of the present invention.

Cap 20 is any device suitably configured to maintain or increase the pressure between the surfaces of pathology by limiting wire 12 movement. As shown in FIGS. 2A-2E, exemplary caps 20 may include various configurations, materials, shapes and/or sizes. In one embodiment, and as shown in FIG. 2A, cap 20 includes an inverse interface component 22 relative to wire 12 interface component such that cap 20 is restricted from backwards translation after cap 20 is inserted over wire 12. In one embodiment, the interface component 22 on cap 20 is located at least on the inside surface of the cap and includes a saw tooth pattern with the same or similar pitch as the saw tooth on wire 12. This configuration also allows cap 20 to slide along wire 12 without the need for spinning cap 20 which is important because time is of the essence in a medical procedure and spinning the cap down a sufficiently long length of wire would be very time-consuming. Examples of cap 20 include a screw cap 20, flat cap 20 and a quick cap 20. As shown in FIG. 2C, screw cap 20 is configured with teeth 22, cutting threads 24 and/or mating threads 26 on the outside surface to facilitate rotating cap 20 into the cortex to, for example, fix surgical plates against certain pathology. However, cutting threads 24 may not be needed on any of the caps because cutting threads 6 of head component 2 may have already tapped the threads on the inside surface of the bone, so the teeth 22 or mating threads 26 alone can simply rotatably engage the threads formed from cutting threads 6 and provide sufficient friction to secure the cap in the bone. As shown in FIG. 2D, flat cap 20 may include teeth 22, cutting threads 24 and/or mating threads 26 on the outside surface to facilitate rotating cap 20 into the cortex, but it also is configured with a flat top surface 28 to allow cap 20 to be inserted into the cortex such that the flat top surface 28 of cap 20 does not substantially protrude from the cortex surface. As best shown in FIG. 2A, for example, the quick cap 20 or any other cap may be configured with only the interface component on the inside surface, thereby allowing for quick and easy assembly.

Figure 2E:
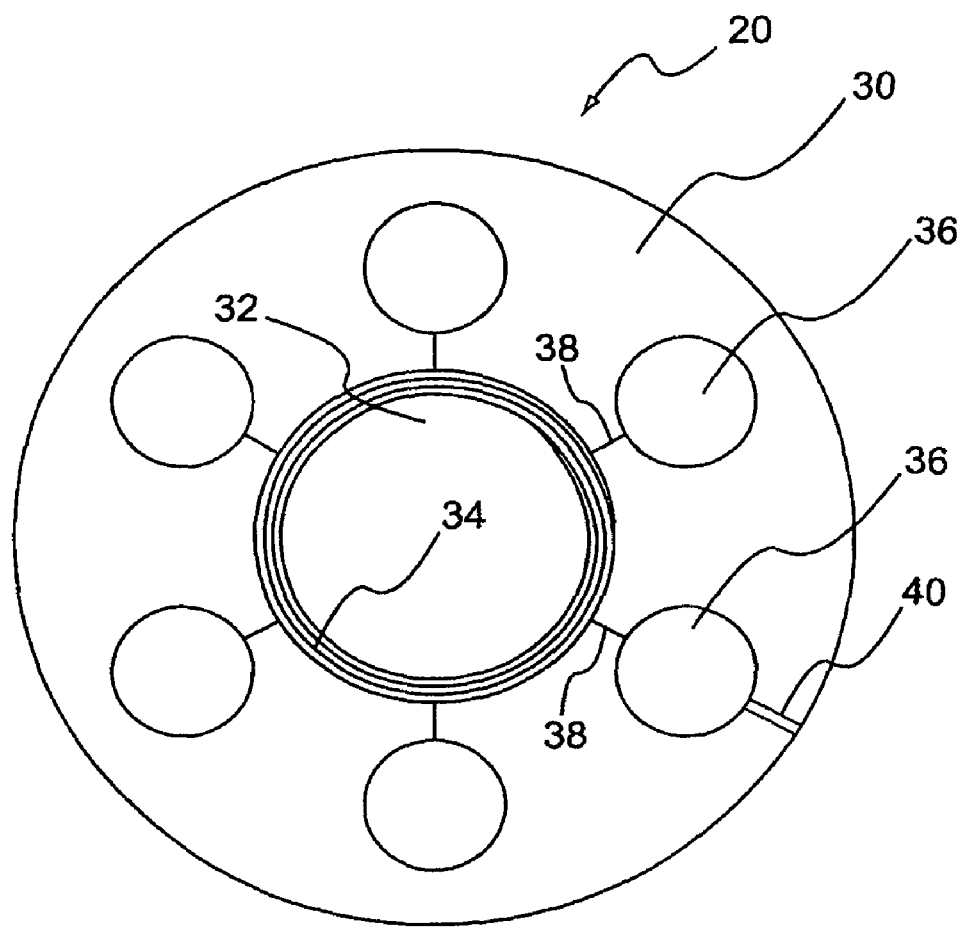
FIG. 2E is a top view of an alternative embodiment of a cap in accordance with an exemplary embodiment of the present invention.

With reference to FIG. 2E, in one embodiment, cap 20 is configured as a planar disk 30 with a center hole 32, wherein the center hole 32 includes an interface component 34 on its inner circumference surface. In an exemplary embodiment, the pitch of the saw tooth interface component is about 0.25 mm-0.5 mm. The planar disk 30 may also include any configuration for facilitating expansion of the disk 36 while sliding down wire 12. The configurations may include, for example, a cut 38 or a hole 36 in the planar disk 30. The planar disk may include multiple holes or cuts spaced over the planar surface. One or more of the additional holes 36 may also be connected to a cut 38 in the planar surface that extends to the center hole 32. One or more of the holes 36 may also be connected to a cut 40 in the planar surface that extends to the outside edge of the planar surface. In one embodiment, six additional holes 36 are evenly spaced around the planar surface with each hole 36 connected to a cut 38 which extends to the center hole, while one hole 36 also includes a cut 40 that extends to the outside edge of the planar surface.

The planar disk may also set inside a shallow cup device, wherein the circumference of the cup is slightly larger than the circumference of the planar ring in order to allow expansion of the ring. Moreover, a spring, or any other device suitably configured to apply pressure to cap 20, is placed between the planar ring and the cup device. In one embodiment, a bellville spring is used to apply pressure to the cap 20. The spring is configured to provide tension on wire 12 after resorption. During the healing process, cartilage forms at the break and the cartilage compresses, so bone resorption typically occurs at the location of the fracture. When tension on the lagwire is released due to bone resorption during healing, in one embodiment, cap 20 allows for auto tightening of the lagwire because micro-motions or vibrations will often cause cap 20 interface device 22 to click down another notch on the inverse interface device of the wire 12.

Figure 3:
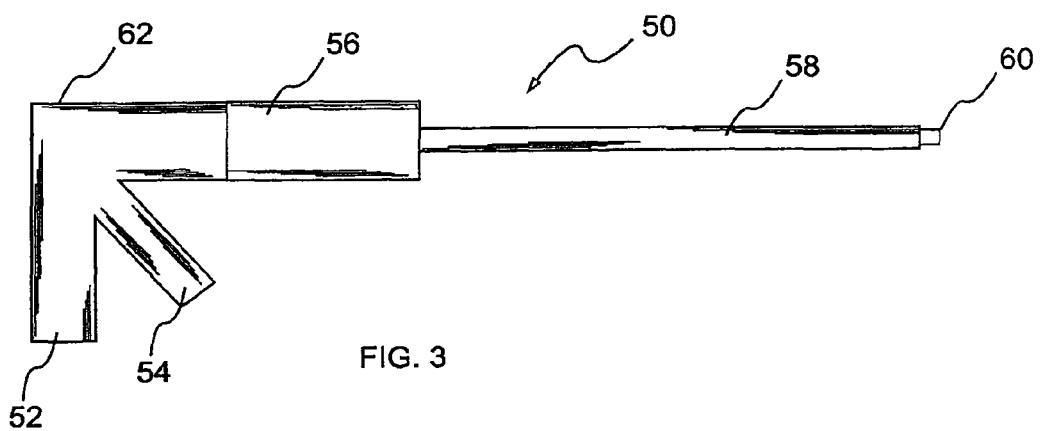
FIG. 3 is a tensioner in accordance with an exemplary embodiment of the present invention.

A tensioner 50 may also be used in conjunction with the present invention. With respect to FIG. 3, the tensioner 50 is any device suitably configured to insert a cap 20 into an object and/or provide tension to a wire 12. In one embodiment, tensioner 50 increases the pressure between the surfaces of pathology by providing tension to a wire 12 while the head component 2 of wire 12 is fixed into a bone or far cortex. In an exemplary embodiment, tensioner 50 includes a handle 52 with a hand trigger 54, wherein the handle 52 supports a rotatable barrel 56 which mates with a cylindrical rod 58. Cylindrical rod 58 may be cannulated to receive wire 12 and/or have a driver 60 (e.g., hex, phillips, screw, allen and/or the like) at its distal end for mating with the tool attachment 10 of head component 2. The barrel 56 may be rotated manually or automatically in order to rotate the driver 60 into the object (e.g., bone or cortex). In one embodiment, tensioner 50 includes a means for exerting a force on wire 12, such as, for example, internal gears, wherein the gears include an interface component (e.g., saw tooth) which mate with the inverse sawtooth on wire 12. By pivoting the hand trigger 54, the internal gears are rotated such that the gears cause wire 12 to translate out the back end 62 of the tensioner 50, thereby exerting tension on wire 12 which is fixed at its distal end. The tensioner 50 may also include a gauge type device or any other device which is suitably configured to measure and/or display the tension exerted on wire 12.

A tensioner 50 may also be used in conjunction with the present invention. With respect to FIG. 3, the tensioner 50 is any device suitably configured to insert a cap 20 into an object and/or provide tension to a wire 12. In one embodiment, tensioner 50 increases the pressure between the surfaces of pathology by providing tension to a wire 12 while the head component 2 of wire 12 is fixed into a bone or far cortex. In an exemplary embodiment, tensioner 50 includes a handle 52 with a hand trigger 54, wherein the handle 52 supports a rotatable barrel 56 which mates with a cylindrical rod 58. Cylindrical rod 58 may be cannulated to receive wire 12 and/or have a driver 60 (e.g., hex, phillips, screw, alien and/or the like) at its distal end for mating with the tool attachment 10 of head component 2. The barrel 56 may be rotated manually or automatically in order to rotate the driver 60 into the object (e.g., bone or cortex). In one embodiment, tensioner 50 includes a means for exerting a force on wire 12, such as, for example, internal gears, wherein the gears include an interface component 66 (e.g., saw tooth) which mate with the inverse sawtooth 20 on wire 12. By pivoting the hand trigger 54, the internal gears 64 are rotated such that the gears cause wire 12 to translate out the back end 62 of the tensioner 50, thereby exerting tension on wire 12 which is fixed at its distal end. The tensioner 50 may also include a gauge type device or any other device which is suitably configured to measure and/or display the tension exerted on wire 12.

After attaching the head component 2 to the bone, the surgical drill is removed and a cap 20 is threaded onto the proximal end 14 of wire 12. Cap 20 is then translated distally along wire 12 until cap 20 contacts the bone or other desired pathology. In one embodiment, a lagwire tensioner is used to exert tension on the lagwire. In another embodiment, a lagwire tensioner 50 may be used to force or seat cap 20 into the bone surface or any other desired position. The hex head 60 of the tensioner 50 may be used to screw cap 20 into the bone surface. In another embodiment, the lagwire tensioner 50 exerts tension on the lagwire 12 up to a desired tension which may be read from a gauge communicating with the tensioner.

After positioning the lagwire device 1 and applying the appropriate amount of tension, in one embodiment, the excess wire 12 may be suitably removed by, for example, a wire cutter or any other suitable device. In another embodiment, a crimp type device may be placed on wire 12 to also help maintain tension. The crimp may include a clamp type device, bending the existing wire 12, screwing a nut onto the end of wire 12 and/or the like. The crimp may be placed on wire 12 after cap 20 is set in place, for example, in order to crimp other end pieces together. The tensioner 50 may also be used to reverse screw cap 20 in order to remove a wire 12 out of the bone. Moreover, in a situation where head component 2 strips out of the bone (for example, when the bone is of poor quality), the present invention allows the lagwire to be pushed through the opposite side of the bone and through the skin such that the head component 2 of wire 12 can be suitably removed (e.g., cut off) and a cap 20 can be placed onto that end of the lagwire, thereby resulting in better purchase (e.g., quality of fixation) of the bone.

Figure 4A:
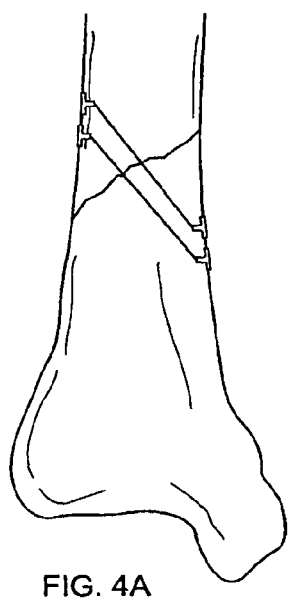
FIG. 4A is a fixation of a bone fracture in accordance with an exemplary embodiment of the present invention.
Figure 4B:
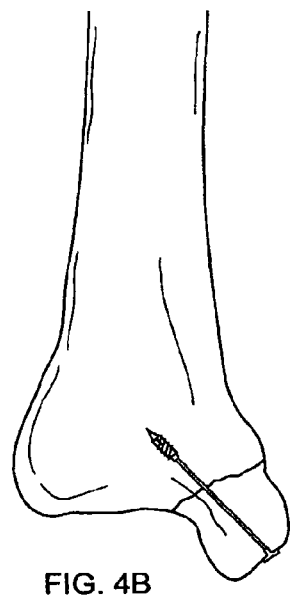
FIGS. 4B-4D are fixations of fractures of a certain portions of a bone in accordance with an exemplary embodiment of the present invention.
Figure 4C:
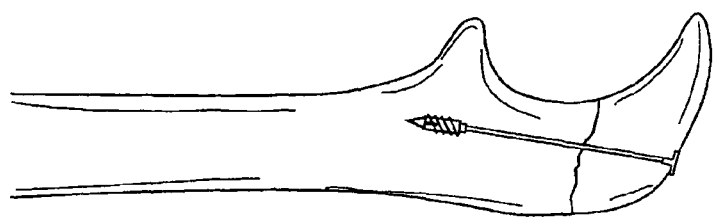
Figure 4D:
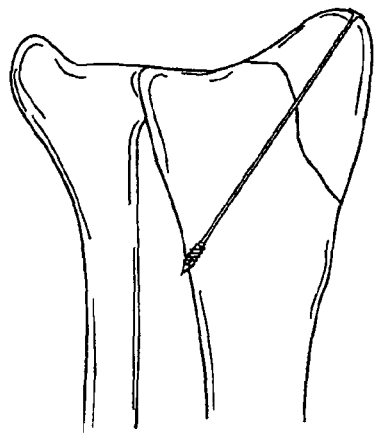
Figure 4F:
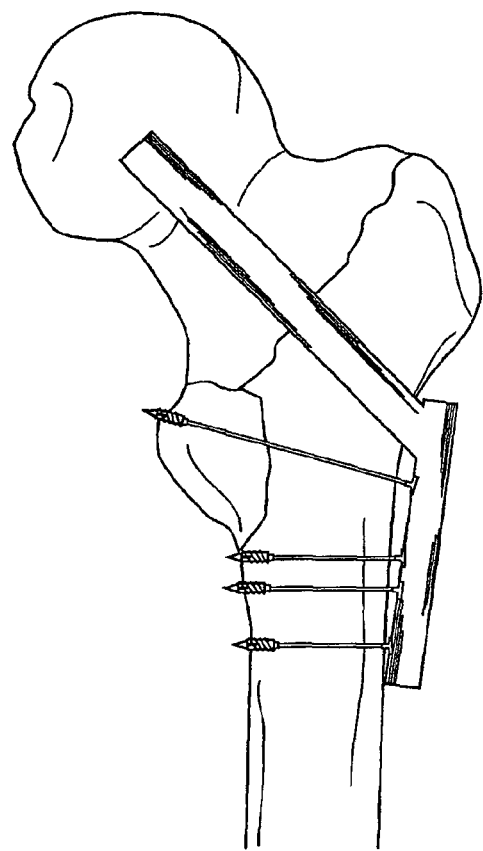
FIGS. 4F-4G is a fixation of a bone fracture by inserting the lagwire through the entire limb to facilitate holding a plate to the bone to help fix certain types of fractures in accordance with an exemplary embodiment of the present invention.
Figure 4E:
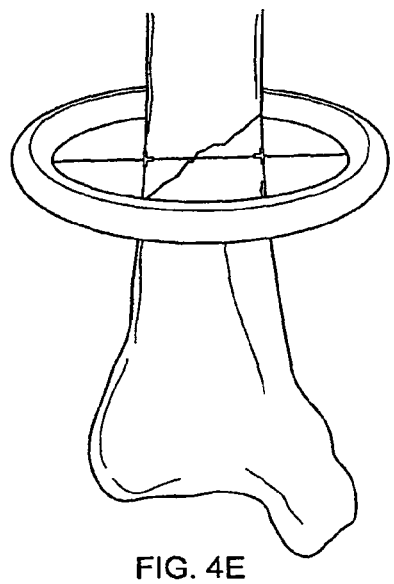
FIG. 4E is a fixation of a bone fracture by inserting the lagwire through the entire limb to facilitate attaching an external fixation device to the limb in accordance with an exemplary embodiment of the present invention.
Figure 4G:
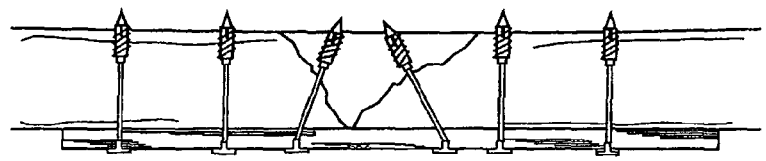

With respect to FIGS. 4A-4G, the lagwire system discussed herein can be used for the fixation of various types of bone fractures. FIG. 4A shows the use of the present invention for an exemplary fixation of a bone fracture or break. FIGS. 4B-4D show the use of the present invention for an exemplary fixation of fractures of certain portions of bones. Moreover, as shown in exemplary FIGS. 4F and 4G, the lagwire system 1 may also be used in a similar manner discussed herein in order to assist in holding a plate to the bone to help fix certain types of fractures. In other types of fractures, the lagwire may be placed through an entire limb to, for example, attach an external fixation device to the limb as shown in exemplary FIG. 4E.

As described herein, the system and method of the present invention provides a device which is self-drilling, self-tapping and can be inserted under power. The invention also facilitates reducing and fixing fractures in one step. As such, the invention substantially expedites the process for fixation of bone fractures which is, of course, critical during trauma situations in order to stabilize a patient or to minimize the amount of time the patient is on the operating table or under anesthesia. In contrast to typical prior art screws wherein a gliding hole in the near cortex simply guides the screw, the present invention provides the ability for two sides of cortex lag screw fixation. Moreover, because of the strength of the attachment to the bone, the invention enables sufficient fixation even in poor quality bone material. Furthermore, wherein the prior art systems often require the use of cannulated screws in order to utilize a guidewire for placement, the present invention does not require the use of cannulated screws. Because the lagwire includes a tip 4 which creates a pilot hole, taps the bone for threads and fixes the threads into the bone, the system and method minimizes the possibility of inaccurate placement into the distal cortex or missing the distal hole.

In prior art systems, the physician typically cuts a relatively large opening in the skin in order to locate the bone segments, pull the bone segments into alignment, then place the screw into the bones. In the present invention, the system facilitates the percutaneus technique by allowing the physician to cut a minor incision into the skin for the head component, insert the head component, then pull the bones together with wire 12 and set the cap, all without large incisions or additional incisions.

The present invention is described herein in connection with the fixation of bone fractures; however, one skilled in the art will appreciate that the lagwire system or method described herein may also be used for changing, maintaining, reducing or expanding the distance between objects or surfaces, compressing objects together or providing pressure to surfaces. For example, the present invention may be used to repair wood products, tree limb damage, breaks in supports or columns, cracks in sculptures or buildings, breaks in sections of concrete or other building materials, cracks or breaks in car parts and/or the like.

In the foregoing specification, the invention has been described with reference to specific embodiments. Various modifications and changes can be made, however, without departing from the scope of the present invention as set forth in the claims below. The specification and figures are to be regarded in an illustrative manner, rather than a restrictive one, and all such modifications are intended to be included within the scope of present invention. Accordingly, the scope of the invention should be determined by the appended claims and their legal equivalents, rather than by the examples given above. For example, the steps recited in any of the method or process claims may be executed in any order and are not limited to the order presented in the claims.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the claims. As used herein, the terms "comprises", "comprising", "includes", "including", or any other variations thereof, are intended to cover a non-exclusive inclusion, such that a process, method, article, or apparatus that comprises or includes a list of elements does not include only those elements but may include other elements not expressly listed or inherent to such process, method, article, or apparatus. Further, no element described herein is required for the practice of the invention unless expressly described as "essential" or "critical."

The invention claimed is:

1. A method for facilitating a change in distance between a first bone portion and second bone portion of a bone fracture, said method comprising:

inserting a head component into said first bone portion, wherein said head component cuts into said first bone portion, wherein said head component includes a tip, cutting threads, fastening threads, and a tool attachment, wherein said head component is affixed to a flexible wire comprised of a thin metal having a first end and a second end, wherein said first end of said flexible wire mates with said head component, said flexible wire having a first interface component along a portion of said wire, wherein said flexible wire is at least one of bendable without the use of tools and is able to be cut with a wire cutter, wherein said cutting threads are operable for insertion into and termination within said first bone portion, wherein said fastening threads are operable for mating with a thread formed by said cutting threads, and wherein said tool attachment is operable to receive a cannulated driver, wherein said first interface component includes a sawtooth configuration having a plurality of sawteeth, wherein said sawtooth configuration is configured such that one side of each tooth is substantially perpendicular to a surface of said wire and the other side of said sawtooth is substantially angular to said surface of said wire;

translating a cap, without rotation of said cap, over said second end of said flexible wire and into said second bone portion, wherein said cap includes threads on an outside surface to facilitate rotating said cap into said second bone portion after said cap is translated over a portion of said flexible wire and said cap is configured to mate with said second end of said wire, wherein said cap is configured to minimize said cap from protruding from said second bone portion, wherein said cap includes a second interface component including an inverse sawtooth configuration on an inner surface of said cap such that said cap is configured to translate along said wire with a portion of said inverse sawtooth configuration sliding over a portion of said sawtooth configuration, wherein said sawtooth configuration and said inverse sawtooth configuration are configured to allow said cap to translate along said wire in only one direction, and wherein said inverse sawtooth configuration includes a plurality of inverse teeth, and wherein said cap includes a center hole for receiving said wire and additional openings for facilitating expansion of said cap; and, tensioning said flexible wire by applying a force on said wire away from said first bone portion and said second bone portion such that said head component pulls said first bone portion toward said second bone portion therefore reducing the distance between said first bone portion and said second bone portion, while said cap minimizes loss of tension in said wire by engaging said sawtooth with said inverse sawtooth.

2. The method of claim 1, wherein said inserting comprises drilling said head component into said first bone portion.

3. The method of claim 1, further comprising removing excess of said flexible wire extending beyond said cap.

4. The method of claim 1, wherein said force is exerted by a tensioner.

5. The method of claim 4, wherein said tensioner comprises a gauge to determine the amount of tension exerted.

6. The method of claim 1, wherein said additional openings for facilitating expansion of said cap are each connected to said center hole via a cut comprising an area of no material on the cap between an outer circumference of each of said additional openings and said central hole.

7. The method of claim 6, wherein said cap comprises a substantially flat top to minimize said cap from protruding from said second bone portion.

* * * * *